United States Patent
MacDougall et al.

(10) Patent No.: US 11,179,035 B2
(45) Date of Patent: Nov. 23, 2021

(54) REAL-TIME REMOVAL OF IR LED REFLECTIONS FROM AN IMAGE

(71) Applicant: Natus Medical Incorporated, Pleasanton, CA (US)

(72) Inventors: Hamish MacDougall, Sydney (AU); Michael Hetner, Tune (DK); Poul-Erik Hansen, Herlev (DK); Mohan Baro, Chicago, IL (US); Thomas Geertsen, Slagelse (DK)

(73) Assignee: Natus Medical Incorporated

( * ) Notice: Subject to any disclaimer, the term of this patent is extended or adjusted under 35 U.S.C. 154(b) by 196 days.

(21) Appl. No.: 16/521,901

(22) Filed: Jul. 25, 2019

(65) Prior Publication Data
US 2020/0029808 A1 Jan. 30, 2020

Related U.S. Application Data

(60) Provisional application No. 62/703,364, filed on Jul. 25, 2018.

(51) Int. Cl.
*A61B 3/12* (2006.01)
*A61B 3/14* (2006.01)
(Continued)

(52) U.S. Cl.
CPC ............... *A61B 3/12* (2013.01); *A61B 3/145* (2013.01); *A61B 5/6803* (2013.01);
(Continued)

(58) Field of Classification Search
CPC ......... A61B 3/12; A61B 3/145; A61B 5/6803; A61B 3/15; A61B 3/113; A61B 5/6821;
(Continued)

(56) References Cited

U.S. PATENT DOCUMENTS 4,102,563 A 7/1978 Matsumura
4,533,223 A 8/1985 Duparchy
(Continued)

FOREIGN PATENT DOCUMENTS

AU 1966001283 8/1967
AU 2011368026 B2 11/2012
(Continued)

OTHER PUBLICATIONS

Bergasa, Luis & Nuevo, Jesús & Sotelo, Miguel-Angel & Barea, Rafael & Guillén, Maria. (2006). Real-time system for monitoring driver vigilance.. IEEE Transactions on Intelligent Transportation Systems. 7. 63-77. 10.1109/ISIE.2005.1529113.
(Continued)

*Primary Examiner* — Mohammed A Hasan
(74) *Attorney, Agent, or Firm* — Widerman Malek, PL; Daniel C. Pierron

(57) ABSTRACT

A system for the real-time removal of reflections from an image including a head wearable device, a first illuminator, a second illuminator, at least one camera and a reflection removal processor. The first and the second illuminators are configured to provide light and to operate one at a time alternately. The at least one camera is configured to capture a first image of the eye of the user when the first illuminator is in an ON state and a second image when the second illuminator is in an ON state. The operation of the at least one camera is synchronized with the operation of the first illuminator and the second illuminator. The camera captures images and transfers them to the reflection removal processor that provides real-time removal of reflections by combining the first image and the second image.

20 Claims, 5 Drawing Sheets

(51) Int. Cl.
*A61B 5/00* (2006.01)
*A61B 3/15* (2006.01)
*A61B 3/113* (2006.01)
*A61B 3/00* (2006.01)

(52) U.S. Cl.
CPC .............. *A61B 3/0008* (2013.01); *A61B 3/113* (2013.01); *A61B 3/15* (2013.01); *A61B 5/6821* (2013.01)

(58) Field of Classification Search
CPC ...... A61B 3/0008; A61B 3/0025; A61B 3/158; A61B 5/1171; G06T 2207/10152; G06T 2207/10048; G06T 5/005; G06T 2207/20221; G06T 5/50; G06K 9/0061
USPC ......................................................... 351/206
See application file for complete search history.

(56) References Cited

U.S. PATENT DOCUMENTS

| | | | |
|---|---|---|---|
| 6,088,470 A * | 7/2000 | Camus | A61B 3/156 382/117 |
| 6,616,277 B1 | 9/2003 | Davenport | |
| 8,325,996 B2 | 12/2012 | Martin | |
| 8,447,087 B2 | 5/2013 | Cuffney | |
| 9,235,762 B2 | 1/2016 | Tosa | |
| 9,398,978 B2 | 7/2016 | Lee | |
| 9,456,746 B2 | 10/2016 | Bublitz et al. | |
| 9,521,950 B2 | 12/2016 | Verdooner | |
| 9,672,387 B2 | 6/2017 | Thorn et al. | |
| 2013/0271728 A1 | 10/2013 | Ranchod | |
| 2014/0184775 A1 * | 7/2014 | Drake | G06F 1/163 348/78 |
| 2015/0371383 A1 | 12/2015 | Chabrier et al. | |
| 2016/0050345 A1 | 2/2016 | Longbotham et al. | |
| 2017/0035293 A1 * | 2/2017 | Nistico | A61B 3/0008 |
| 2017/0086667 A1 | 3/2017 | Zhou | |
| 2017/0164830 A1 | 6/2017 | Huang | |

FOREIGN PATENT DOCUMENTS

| | | |
|---|---|---|
| AU | 2015221480 A1 | 4/2016 |
| CA | 2487411 A1 | 12/2003 |
| CA | 2836048 A1 | 12/2012 |
| CA | 2906828 A1 | 9/2014 |
| CN | 1761078 A | 4/2006 |
| EP | 1241614 A2 | 9/2002 |
| EP | 2136550 A2 | 6/2009 |
| EP | 2777593 A2 | 3/2014 |
| JP | 2006106006 | 11/2005 |
| JP | 2008246004 | 10/2008 |
| JP | 2009254525 | 11/2009 |
| JP | 2016093253 | 12/2014 |
| KR | 1020157021052 | 9/2015 |
| KR | 1020167016972 | 8/2016 |
| WO | 1999038121 A1 | 7/1999 |
| WO | 2000067635 A1 | 11/2000 |
| WO | 2003031923 A1 | 3/2002 |
| WO | 2003029769 A1 | 4/2003 |
| WO | 2015126466 A1 | 8/2015 |

OTHER PUBLICATIONS

Lee, J.W.; Heo, H.; Park, K.R. A Novel Gaze Tracking Method Based on the Generation of Virtual Calibration Points. Sensors 2013, 13, 10802-10822.

Xiong, Jianbin & Xu, Weichao & Liao, Wei & Wang, Qinruo & Liu, Jianqi & Liang, Qiong. (2013). Eye Control System Base on Ameliorated Hough Transform Algorithm. Sensors Journal, IEEE. 13. 3421-3429. 10.1109/JSEN.2013.2262934.

* cited by examiner

REAL-TIME REMOVAL OF IR LED REFLECTIONS FROM AN IMAGE

PRIORITY

This application claims priority from the U.S. provisional application having Ser. No. 62/703,364, filed Jul. 25, 2018. The disclosure of that provisional application is incorporated herein by reference as if set out in full.

BACKGROUND OF THE DISCLOSURE

Technical Field

This invention relates generally to the field of digital image processing. More particularly, this invention relates to a system and method that removes reflections or hotspots from an image captured by a camera.

Description of the Related Art

Images of the eye may be utilized both for medical purposes and biometric purposes. Many conventional devices have thus been designed to capture images of the eye for these and other reasons. For such purposes, the quality of the image must be high and precise. The phenomenon of bright spots and shadows appearing in images taken by a camera of a subject under one or more lights or other illuminators is well known. Their presence may be considered to be an inconvenience or as rendering an image unacceptable for its intended purpose.

Varying imaging techniques have been developed for capturing the image of the eye, but one common feature in those that obtain a highly precise image is that the eye is illuminated with an illumination source at the time of taking the image. One drawback to such methods is that a portion of the illuminated light beam is reflected outward from the surface of the eye, thereby creating a hotspot devoid of eye detail on the image captured. The occurrence of such hotspots can cause various challenges in diagnosing or pupil tracking because the hotspot can be misinterpreted by computer algorithms and tracking software. For instance, if the center of mass of the eye or pupil is obtained for tracking purposes, the hotspot can disrupt the data such that the true center of mass is not detected. Thus, for improved diagnoses of the eye, the appearance of hotspots must be removed from the images captured. Some systems and methods have been developed to avoid or minimize the appearance of hotspots on the image. Many of these prior art methods are quite time consuming, taking several minutes or even hours to complete.

One of the currently available systems provides a fundus camera free from undesired reflected and diffused light beams. The fundus camera avoids undesired light beams reflected primarily from the surface of the cornea by means of a ring illumination method. However, this method only focuses on removal of reflected light from the cornea and nothing is done to remove the reflection of light beams from the lens. Another method and apparatus describes removal of bright or dark spots by the fusion of multiple images. In this method, a composite image of the subject is formed by selecting pixels based upon their gray scale values or using pyramid image processing. However, this method requires multiple illumination sources for producing multiple images of the subject each created under illumination by different illuminators. Another apparatus and method for imaging an eye sections images and focal planes and utilizes an illumination system that uses one or more LEDs, shifting optical elements, flipping masks, and/or aperture stops where the light can be delivered into the optical imaging system on optical axis or off axis from center of optical imaging system and return imaging path from the eye, creating artifacts indifferent locations on the eye image. However, the sectioning of images and focal planes, shifting optical elements, flipping masks interfere with adequate quality eye image sections.

Therefore, there is a need for a system and method that provides the real-time removal of hotspots from an image captured by a camera. Such a system and method would focus on removal of reflected light from every portion of the eye to obtain a clear image that may be utilized for diagnosis or biometric access. Such a system would require only two illuminators to provide lighting to the system. Further, this system and method would require less time for removal of bright or dark spots by combining two images. The present embodiment overcomes shortcomings in this area by accomplishing these critical objectives.

SUMMARY OF THE DISCLOSURE

To minimize the limitations found in the existing systems and methods, and to minimize other limitations that will be apparent upon the reading of this specification, the preferred embodiment of the present invention provides a system and method for real-time removal of reflections from an image.

The system comprises an eye wearable device, a first illuminator, a second illuminator, at least one camera and a hotspot removal processor. The eye wearable device is adaptable to be removably attached to the subject or user. The eye wearable device may be selected from a group consisting of glasses, goggles, a helmet, or any other suitable eye wearable device. The first and second illuminators are positioned at a distance therebetween and attached to an inner side of the eye wearable device. The first and second illuminators can be infrared light emitting diodes (IR LEDs) or any other light source. In the preferred embodiment, each of the at least two illuminators of the system is configured to operate one at a time.

The at least one camera is configured to capture a first image of the eye of the user when the first illuminator is in the ON state and the second illuminator is in the OFF state and a second image is captured when the first illuminator is in the OFF state and the second illuminator is in the ON state. Thus, a first image is captured when the first illuminator is in the ON state and the second image is captured when the second illuminator is in the ON state. By sequential operation of the first illuminator and the second illuminator, a sequence of images of the eye is formed. In alternate embodiments, a video may also be taken. The sequence of images or video is transferred to the reflection removal processor. The reflection hotspot removal processor is in communication with the camera. The camera may be connected to the reflection hotspot removal processor by means of a cable. The reflection hotspot removal processor is adaptable to receive the sequence of images captured by the at least one camera.

As the first illuminator and the second illuminator are configured to operate alternatively and as the camera is synchronized with the operation of the first illuminator and the second illuminator, the sequence of images contains the first image, the second image, then again the first image, the second image and likewise. The reflection removal processor is configured to combine the first image and the second image which are alternatively illuminated by the first illuminator and the second illuminator. In the reflection removal processor, two adjacent images, for example, the first image and the second image are combined to remove reflections. For combining the images, the system selects areas from the first image and the second image that exhibit minimal or no reflection. The reflection removal processor then iterates through the first image and the second image pixel by pixel. The minimum pixel value from the first image and the second image are selected and combined together to obtain a combined image free from reflections. The combined image, which is free from reflection or hotspots, is displayed on a monitor and may be used for pupil detection.

The method for real-time removal of reflections from the image utilizing the system for real-time removal of reflections comprises the steps of providing a system for real-time removal of reflections having an eye wearable device, a first illuminator, a second illuminator, at least one camera and a reflection removal processor; capturing a first image by the at least one camera, while the first illuminator is turned ON and the second illuminator is in OFF state. Then capturing a second image by the at least one camera, while a first illuminator is turned OFF and the second illuminator is in ON state. Next, forming a sequence of the first image and the second image by synchronizing the operation of the first illuminator and the second illuminator with the at least one camera. Then, transferring the sequence of images to the reflection removal processor, which combines the first image and the second image having a minimum pixel value by iterating through the first image and the second image pixel by pixel, and finally displaying the combined image without any reflections on a monitor of the reflection removal processor.

A first objective of the present embodiment is to provide a system and method that provides real-time removal of reflections or hotspots from an image captured by a camera.

A second objective of the present embodiment is to provide a system and method that focuses on removal of reflected light from every portion of the eye to obtain a clear image that may be utilized for diagnosis or biometric matters.

A third objective of the present embodiment is to provide a method and system that eliminates the need for complex structures and multiple illumination sources for producing an artifact-free image.

Another objective of the present embodiment is to provide a method and system that requires only or a minimum of two illuminators for providing lighting to the system, although additional illuminators remain possible.

Another objective of the present embodiment is to provide a method and system that by combining images requires less time for removal of bright or dark spots in the images.

These and other advantages and features of the present invention are described with specificity so as to make the present invention understandable to one of ordinary skill in the art.

BRIEF DESCRIPTION OF THE DRAWINGS

In order to enhance their clarity and improve understanding of the various elements and embodiments of the invention, elements in the figures have not necessarily been drawn to scale. Furthermore, elements that are known to be common and well understood to those in the industry are not depicted in order to provide a clear view of the various embodiments of the invention, thus the drawings are generalized in form in the interest of clarity and conciseness.

DETAILED DESCRIPTION OF THE INVENTION

In the following discussion that addresses a number of embodiments and applications of the present invention, reference is made to the accompanying drawings that form a part hereof, and in which is shown by way of illustration of specific embodiments in which the invention may be practiced. It is to be understood that other embodiments may be utilized, and changes may be made without departing from the scope of the present invention.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

As used herein, the singular forms "a", "an" and "the" include plural referents unless the context clearly dictates otherwise. "And" as used herein is interchangeably used with "or" unless expressly stated otherwise. As used herein, the term "about" means +/−5% of the recited parameter. All embodiments of any aspect of the invention can be used in combination, unless the context clearly dictates otherwise.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "wherein", "whereas", "above", and "below" and words of similar import, when used in this application, shall refer to this application as a whole and not to any particular portions of the application.

The description of embodiments of the disclosure is not intended to be exhaustive nor to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Figure 1A:
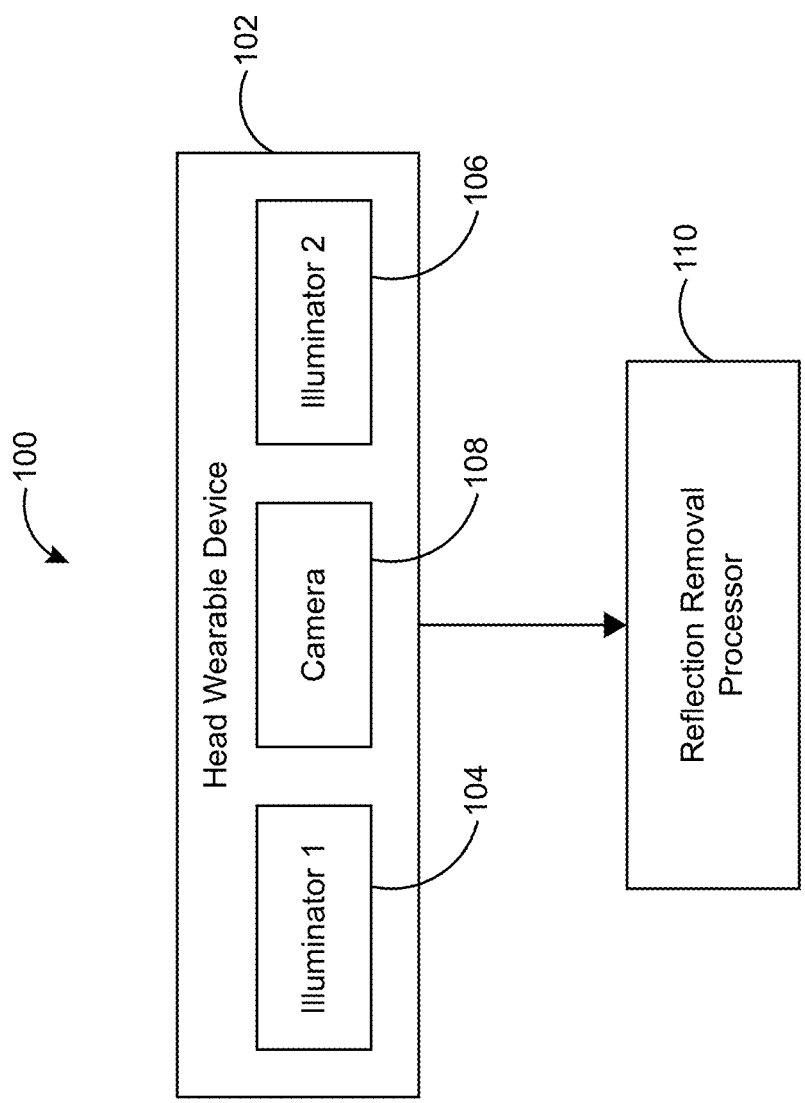
FIG. 1A depicts a schematic diagram of a system for real-time removal of reflections from an image in accordance with the preferred embodiment of the present invention.
Figure 1B:
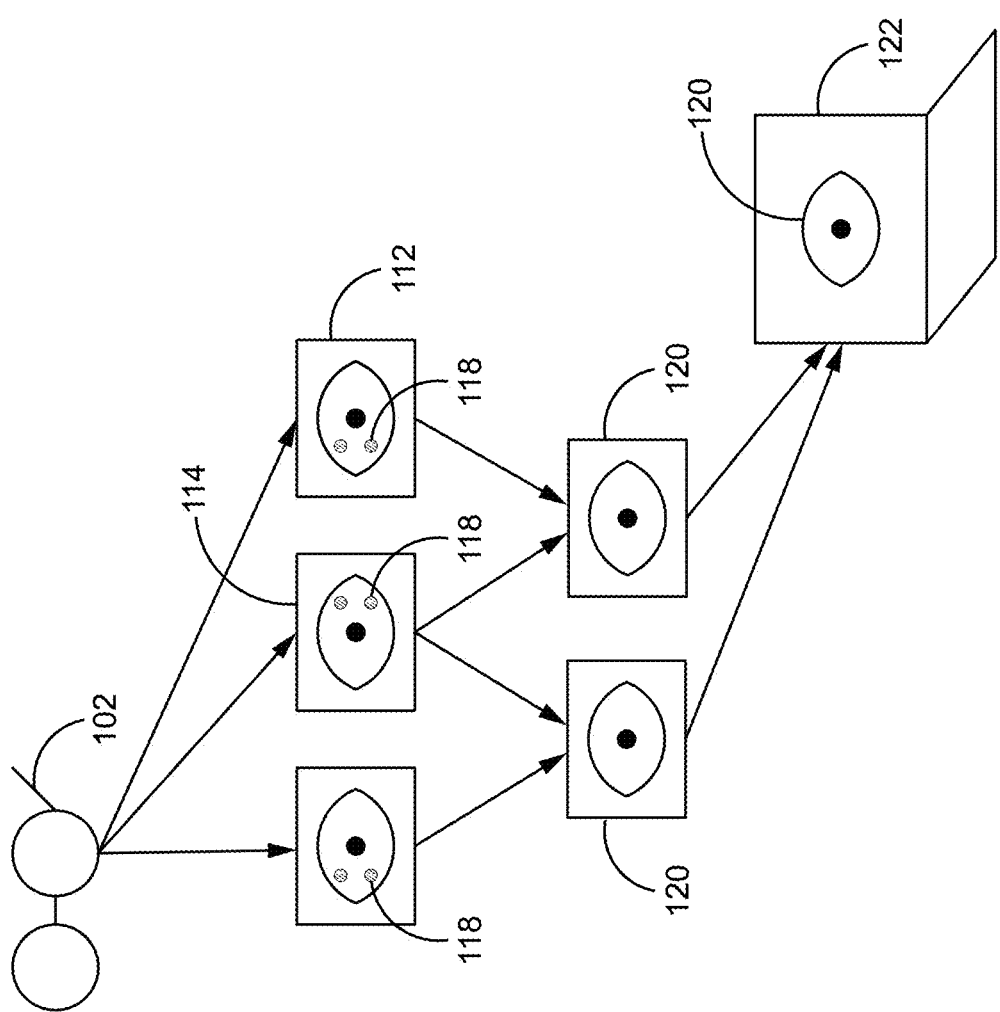
FIG. 1B depicts a schematic diagram of the operation of the system of FIG. 1A in accordance with the preferred embodiment of the present invention.

Referring to FIGS. 1A and 1B, a schematic diagram of a system for real-time removal of reflections from an image 100 is illustrated. The system 100 is utilized for the removal of reflection 118 or hotspots from an image of an eye. The system 100 for real-time removal of reflections 118 from an image of the eye of a user comprises an eye wearable device 102, a first illuminator 104, a second illuminator 106, at least one camera 108 and a reflection removal processor 110 as illustrated in FIG. 1A. The eye wearable device 102 is adaptable to removably attach to the eye of the user. The eye wearable device 102 can be selected from a group consisting of: glasses, goggles, helmets and other suitable eye mountable devices capable of performing the functions described herein.

In one embodiment, illumination sources may comprise a first illuminator, a second illuminator, and the like. In some embodiments, the eye is illumined with an illumination source driven by a source of electrical power (e.g., a separate battery source, power from an outlet, solar power, and the like). It should be appreciated that said illumination source is preferably configured to produce light at selected wavelengths and intensities. For example, the illumination source may comprise one or more light-emitting diodes or other illumination sources and the illumination source may also use fiber optic cables to deliver light. The illumination sources (e.g., LEDs) may be of colors white, red, infrared, blue, green, or any combination of colors, including monochromatic lights in the white, red, infrared, blue, green, or a similar wavelength spectrum. The illumination source may alternatively comprise or incorporate monochromatic lights in any combination of colors or patterns. The illumination source can also be controlled through various means well known in the art, including circuitry within the optical imaging system and/or through a wireless connection coupled with the optical imaging system.

The first illuminator 104 and the second illuminator 106 are positioned at a distance therebetween and attached to an inner side (not shown) of the eye wearable device 102. The first illuminator 104 and the second illuminator 106 are positioned at a distance to prevent overlap of reflections 118 from the eye. This enables the reflections 118 formed by the first illuminator 104 and the second illuminator 106 to be at different positions. The inner side (not shown) of the eye wearable device 102 faces the eye of the user. The first illuminator 104 and the second illuminator 106 are light sources adaptable to provide light towards the eye of the user. The first illuminator 104 and the second illuminator 106 may consist of infra-red light emitting diodes (IR LEDs) or any other light source as described above, and are configured to operate one at a time alternately. Further, a controller may be attached to the camera and the illuminators for turning on a selected illuminator whenever the camera captures an image of the subject.

Figure 2:
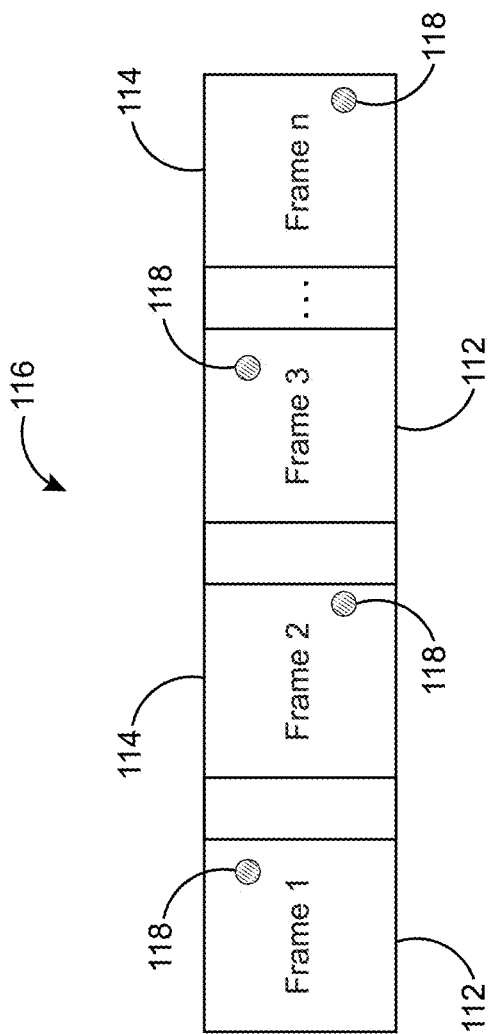
FIG. 2 shows a schematic representation of the sequence of images captured by the operation of the system of FIG. 1A in accordance with the preferred embodiment of the present invention.

The at least one camera 108 is attached to the inner side (not shown) of the eye wearable device 102. The at least one camera 108 is configured to capture a first image 112 of the eye when the first illuminator 104 is in ON state and the second illuminator 106 is in OFF state and a second image 114 is captured when the first illuminator 104 is in OFF state and the second illuminator 106 is in ON state. Thus, only one of the two illuminators 104, 106 functions at a time when the other is in the OFF state. Thus, the first image 112 is captured when the first illuminator 104 is in ON state and the second image 114 is captured when the second illuminator 106 is in ON state. By continuous operation of the first illuminator 104 and the second illuminator 106 alternatively, a sequence of images 116 of the eye is formed as illustrated in FIG. 2. The reflection removal processor 110 is in communication with the camera 108. The camera 108 may be connected to the reflection removal processor 110 by means of a cable (not shown). One embodiment of the present invention may employ illuminators or other light sources with some other camera systems, other than the eye wearable device 102. For example, one embodiment may employ illuminators or other light sources on standard cameras that are not necessarily eye wearable devices.

The reflection removal processor 110 is adaptable to receive the sequence of images 116 captured by the at least one camera 108. The sequence of images 116 is transferred to the reflection removal processor 110. As the first illuminator 104 and the second illuminator 106 are configured to operate alternatively and as the camera 108 is synchronized with the operation of the first illuminator 104 and the second illuminator 106, the sequence of images 116 contains the first image 112, the second image 114, then again the first image 112, the second image 114 and so forth. The synchronization of the first illuminator 104 and the second illuminator 106 with the camera 108 allows the opening of the shutter of the camera 108 when the first illuminator 104 is turned ON and closing of the shutter of the camera 108 when the first illuminator 104 is turned OFF. A time lag is experienced between the turning OFF of the first illuminator 104 and the turning ON of the second illuminator 106. This lag in time prevents overlap of the first image 112 with the second image 114. Similarly, the shutter of the camera 108 opens when the second illuminator 106 is turned ON and closes when the second illuminator 106 is turned OFF. In this manner n number of images can be captured, for example, from frame 1 to frame n as illustrated in FIG. 2.

Thus, it is clear that the operation of the first illuminator 104 and the second illuminator 106 forms the sequence 116 having the first image 112 and the second image 114 alternatively. The reflections or the hotspot formed on an image by any light source positioned at one location is different from the reflection or hotspot formed by the any illuminator positioned at another location. As the first illuminator 104 and the second illuminator 106 are positioned at a distance, the reflection 118 formed on the first image 112 by the first illuminator 104 is at a different position with respect to the reflection 118 formed on the second image 114 by the second illuminator 106. The reflection removal processor 110 is configured to combine the first image 112 and the second image 114 which are alternatively illuminated by the first illuminator 104 and the second illuminator 106.

The operation of the system for the real-time removal of reflection 100 is illustrated in FIG. 1B. In operation, the at least one camera 108 is synchronized with the operation of the first illuminator 104 and the second illuminator 106 captures the first image 112 and the second image 114 of the eye respectively. By the continuous operation of the first illuminator 104 and the second illuminator 106, a sequence of images 116 is captured by the camera 108. These images 116 are transferred to the reflection removal processor 110. In the reflection removal processor 110, two adjacent images, for example, the first image 112 and the second image 114 are combined to remove reflections 118. For example, due to synchronization of the camera 108 with the operation of the first illuminator 104 and the second illuminator 106, as soon as one image reaches the reflection removal processor 110, it is combined with the previous image to form an image free of reflections.

When combining the images, the system 100 selects areas from the first image 112 and the second image 114 that do not have any or at the most have minimal reflection 118 of the first illuminator 104 and the second illuminator 106. The reflection removal processor 110 iterates through the first image 112 and the second image 114 pixel by pixel. The minimum pixel value from the first image 112 and the second image 114 are selected and combined together to get a combined image 120 free from reflections 118. The combined image 120 which is free from reflection 118 is displayed on a monitor 122 and can be used for pupil detection. The method of combining the first image 112 and the second image 114 that does not have any or at the most have minimal reflection 118 is called the minimum gray level method. This method involves processing the first image 112 and the second image 114 utilizing a matrix operation. For example, if the first input image corresponds to A and the second input image corresponds to B (each having a size of W×H), then the matrix level image processing operation is performed by the operator CvMin( ) In this method, two images are given as arguments to the matrix level image processing operator CvMin( ) which provides a resultant image R (of size W×H) that is the minimum of pixels from the first input image A and the second input image B using pixel by pixel terminology. The resultant image R without reflections is given by the equation:

$$R = CvMin(A,B)$$

In one embodiment, the reflection removal processor 110 iterates through the first image 112 and the second image 114 pixel by pixel. Then a weighted sum of the pixels is selected to combine the first image 112 and the second image 114 to obtain a brighter combined image 120 without reflection and with an optimal signal to noise ratio. In this embodiment, the first image 112 and the second image 114 are processed via matrix operations. For example, the first input image A and the second input image B (each having a size of W×H) is processed by the matrix level image processing operation utilizing the operators CvMin( ) and CvMax( ) The first input image A and the second input image B are given as arguments to the operators CvMin( ) and CvMax( ) The operator CvMin( ) provides the minimum pixel value output image C and the operator CvMax( ) provides the maximum pixel value output image D (each having a size of W×H). The difference between the minimum pixel value output image C and the maximum pixel value output image D is determined and given by S. See FIG. 4 for additional detail, and wherein:

$$\text{Difference } \delta = C - D$$

The weight of the minimum pixel value output image C is calculated and given by α, where n is the order of the weighting function.

$$\alpha = \delta^{(n)}$$

The weight of the maximum pixel value output image D is calculated and given by β.

$$\beta = 1 - \alpha$$

The resultant output image R (of size W×H) without any reflections and having optimal signal to noise ratio is given by the following equation:

$$R = C\alpha + D\beta$$

Thus, the synchronization of the first illuminator 104 and the second illuminator 106 with the camera 108 allows for the complete removal of reflections 118 from the image.

In another embodiment, an image may comprise a matrix of pixels each having a gray scale value. Depending upon the size of an image there may be hundreds or even thousands of pixels arranged in an array. Each pixel has a unique x,y coordinate position. Therefore, if there are two images of the same subject there will be one pixel in each image that corresponds to a single point on the subject. If the two images were taken under different lighting conditions the gray scale value of the pixel in the first image that corresponds to a selected point on the subject may be different from the gray scale value of the pixel in the second image that corresponds to the same point. In one example, Image 1 and Image 2 are taken under different lighting conditions which creates a bright spot in each image. The bright spot is represented by the open circles in FIG. 1B. The bright spot in each image has obscured a portion of the subject. Therefore, we select a pixel from either Image 1 or Image 2 for each pixel position, or x,y coordinate position, in the six by six array to form the Final Image in FIG. 1B.

In Image 1 and Image 2 the same pixel's location in both images corresponds to the same unique point on the subject. It may happen that two images are presented where this is not true. Should one image be off center relative to the other image, it is necessary to preprocess one or both images so that a proper pairing can be made. There are several techniques that are well known to those skilled in the art which will accomplish this preprocessing. In the discussion that follows we assume that there has been minimal movement of the subject during the time from capture of the first image to capture of the second image, or that some preprocessing has occurred, to ensure that each physical point on the subject appears at the same (x,y) position in both images.

Normal video images or a set of still images are made up of lines of pixels called raster lines. These raster lines can be consecutively numbered and grouped into two fields. One field contains the odd raster lines and the second field contains the even raster lines. If a first illuminator and a second illuminator are alternately illuminated at the same frame rate as the camera, then one field for a single image will have been created with the first illuminator activated and the other field for that image will have been created with the second illuminator activated. Consequently, if images are available, we can select the even field as our first image and the odd field as our second image or vice versa. If this is done we assume that adjacent pairs of pixels in the video image, one set of pixels from an odd raster line and the other pixel set from an even raster line, correspond to a single unique point on the subject.

One can consider the two initial images as image A and image B with the final composite image being image C. If the first image has pixel values A(x,y) where x and y are coordinates of a two-dimensional, orthogonal coordinate system for specifying the position of pixels in the view of the camera, and the second image has pixel values B(x,y), then the composite image created in accordance with our method has pixel values C(x,y)=MIN(A(x,y), B(x,y)) where MIN is the minimum function that selects the least of its two parameters. We have observed that most, if not all, pixels which represent a hotspot have a gray scale value. As described above, by selecting a minimum gray scale we effectively remove the hotspots from the image. Shadows can be removed by selecting pixels having a maximum gray scale value. However, to avoid selection of pixels that represent hotspots or saturation we select the maximum gray scale value that is below a threshold gray scale value.

Figure 4:
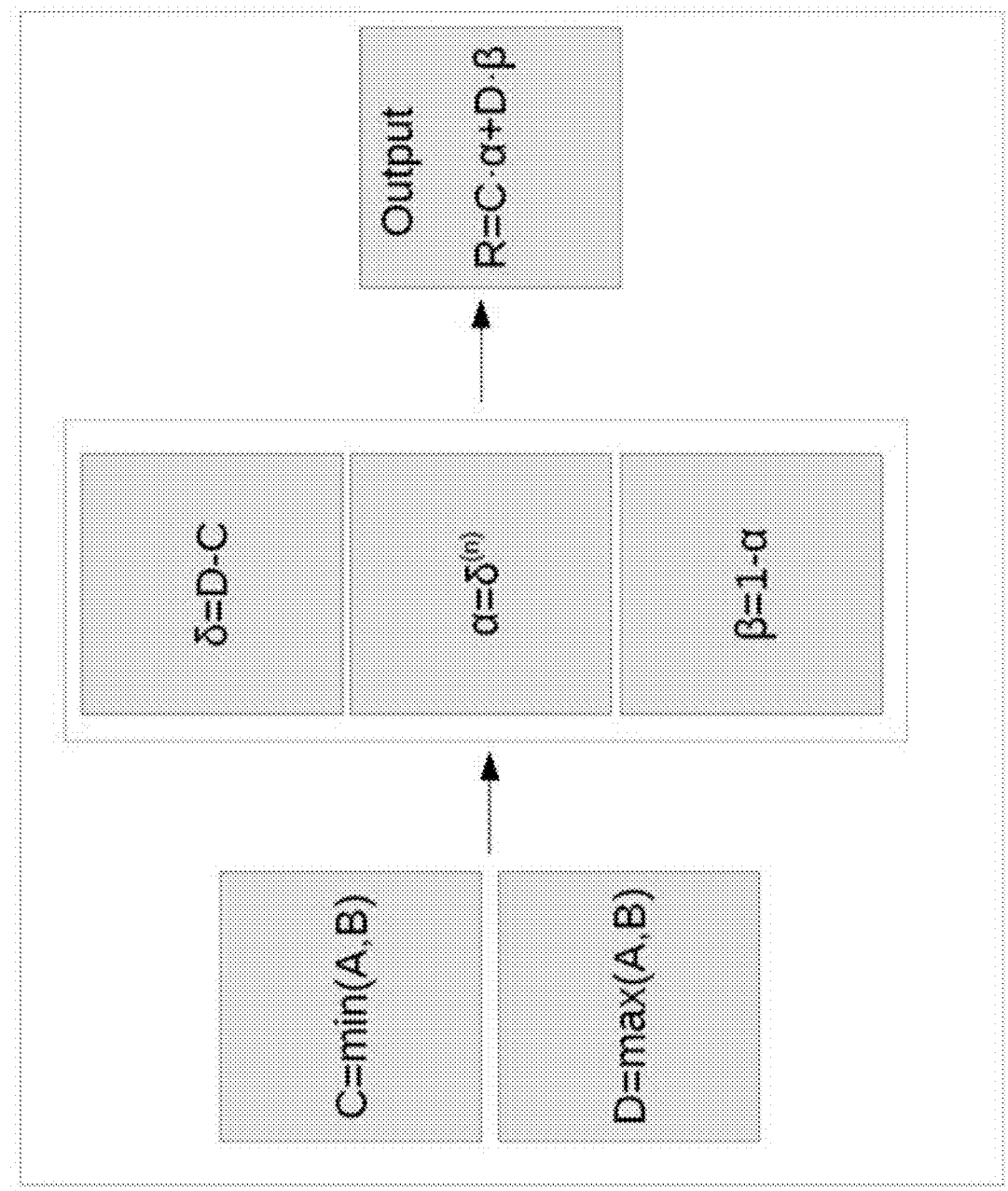
FIG. 4 Shows a portion of a flowchart associated with a weighted sum method utilizing matrix operations.

The proposed method, referred to in the alternate as the weighted sum method as shown in FIG. 4, also overcomes any blooming that may occur. Indeed, the values of pixels surrounding the area of the specular reflection may be corrupted by the saturated pixels (i.e., "blooming"). This occurs because the pixels of charge-coupled devices (CCDs), the most common electronic imagers, are not well isolated from one another. As shown in FIG. 1A, as long as the two light sources are sufficiently separated so that the image and its associated blooming does not overlap image and its associated blooming, every portion of the subject is clearly visible in at least one of the first image or the second image. Hence, every portion of a person's iris and/or cornea can be clearly seen.

The light sources may be implemented with one or more high-power light-emitting diodes, a laser diode fed through an optical fiber, a laser fitted with a diverging lens, an incandescent lamp, or any other source that produces sufficient power with appropriate emission pattern in the appropriate spectral band. The light sources may produce visible light or non-visible light such as infrared.

Although FIG. 1A shows two light sources arranged horizontally, two or more light sources may be arranged horizontally, vertically, radially, or in any other geometry so long as the spacing of the light sources is sufficient for the images of the sources reflected from an eye in the camera's view are separated far enough so that the illumination controller can use one or more of the sources to sufficiently illuminate each portion of the iris and/or cornea without an obscuring specular reflection or blooming in at least one of the multiple images to be used to form the composite output image. Uniquely, only two light sources are required in the present disclosure.

Figure 3:
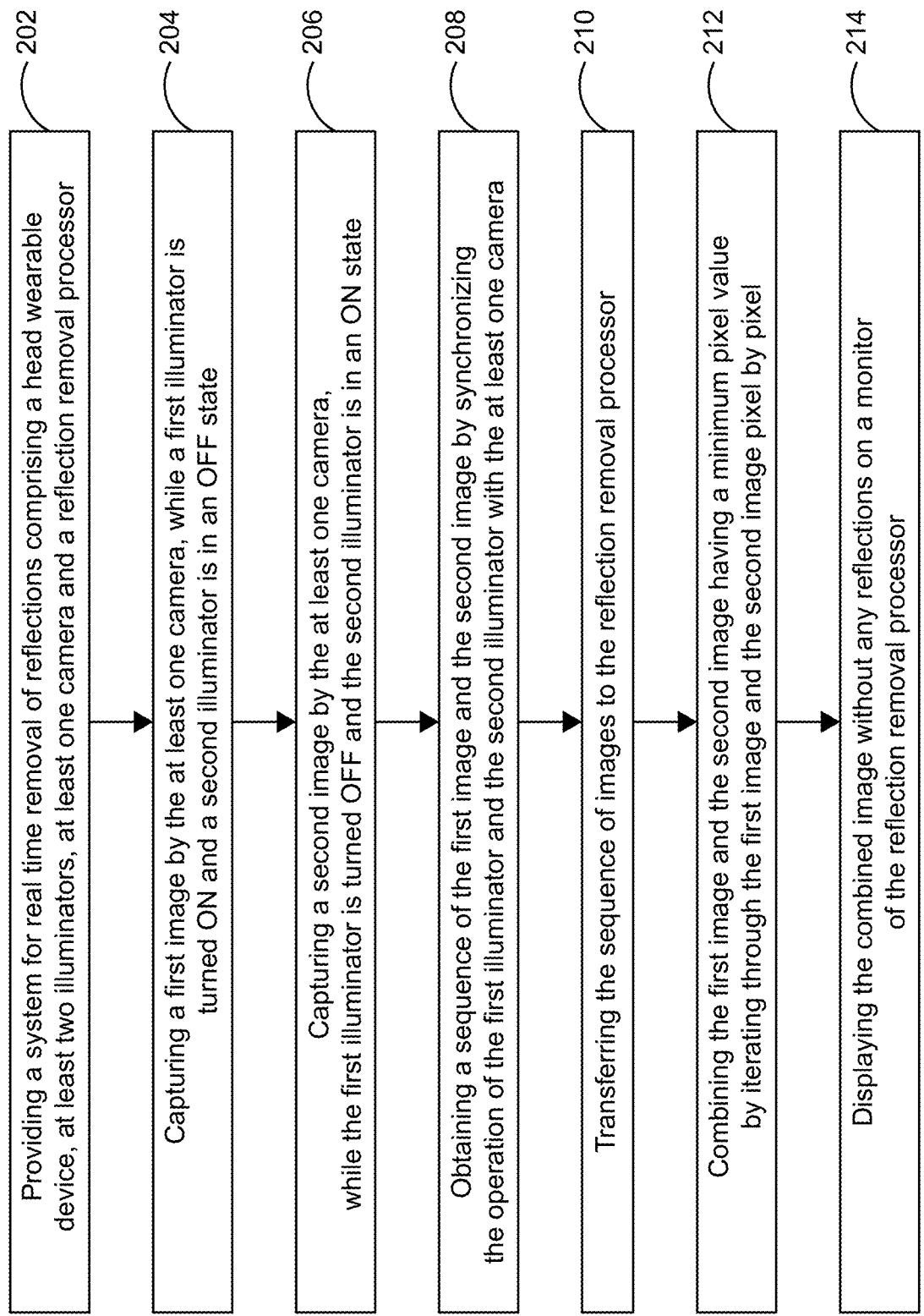
FIG. 3 shows a flow chart of a method for real-time removal of reflections from the image utilizing the system for real-time removal of reflections in accordance with the preferred embodiment of the present invention.

FIG. 3 illustrates a flow chart of a method for real-time removal of reflection hotspots from an image utilizing the system for real-time removal of reflection hotspots of FIG. 1A. The method comprises the steps of: providing a system for real-time removal of reflections having an eye wearable device, a first illuminator, a second illuminator, at least one camera and a reflection removal processor as indicated in block 202. Capturing a first image by the at least one camera, while the first illuminator is turned ON and the second illuminator is turned OFF as indicated in block 204. Then capturing a second image by the at least one camera, while the first illuminator is turned OFF and the second illuminator is turned ON as indicated in block 206. As indicated in block 208, forming a sequence of the first image and the second image is feasible by synchronizing the operation of the first illuminator and the second illuminator with the at least one camera. Transferring the sequence of images to the reflection removal processor is indicated at block 210. Combining the first image and the second image having minimum pixel value by the reflection removal processor by iterating through the first image and the second image pixel by pixel is indicated in block 212 and displaying the combined image without any reflections on a monitor of the reflection removal processor is indicated in block 214.

A hotspot group may be created by one or more individual illuminators, although only two illuminators are required. The minimum number of illuminators and thus hotspot groups with which the function of this system is applicable is two, provided these hotspot groups are non-overlapping (i.e. only one group is visible on a given frame and the hotspot maximas do not touch each other in a combined frame). There is no upper limit to the number of hotspot groups. In some embodiments, where there are more than two hotspot groups as defined above, the system may iteratively remove the hotspot groups using the high order weighted function method by the application of the method on a pair of hotspot groups at a time, i.e., on a pair of frames at a time, each frame containing a single hotspot group. The higher order weighting function method may be modified to enhance the signal to noise ratio of the resultant hotspot free image frames by further fusing consecutive hotspot free image frames for best high dynamic range image.

In yet another embodiment we use two illuminators, a camera, and a reflection removal processor. The eye is illuminated by a first light source and a second light source. The emission patterns of the light sources are such that either of them generates illumination that is fairly even across the front surface of the eye with sufficient intensity for the camera to record a good image of the eye.

Instead of leaving both light sources n on during the time that a subject is present, the light sources are pulsed or flashed in synchronization with the exposure times of the camera 108. Both the intensity and duration of these pulses are controlled to get the correct exposure of the images of the eye.

At least one light path from an illuminator 104 to the camera 108 produces a specular reflection from a first surface (front or back) of the lens. Similarly, at least one light path from an illuminator 106 to the camera 108 produces a specular reflection from the same first surface of the lens and thus generates an image of the illuminator 106 that is visible to a camera 108 as seen in the camera's view of an eye. Although only one pair of images is generated by a first surface of a lens, the second surface of the lens will normally generate another pair of images. These images act the same as the images caused by the first surface in all material respects. Both images may obscure portions of the iris and/or cornea of the eye in the view of the camera 108. Therefore, the controller will turn off the first illuminator 104 which causes the image, while continuing to activate the second illuminator 106, during exposure of a first image. Immediately thereafter, the controller will turn off the second illuminator 106 which causes the image, while continuing to activate the first illuminator 104, during exposure of a second image. From these two images the system forms the composite image using an image processor 110. That composite image is formed from the first image and the second image by the system selecting a pixel from corresponding locations in the first and second images at each pixel location based upon gray scale values of the pixels. This can be more easily understood by referring to FIG. 1B.

In another embodiment, an eye wearable device is disclosed that is adaptable to removably attach to the eye and/or head of the user. Said eye wearable device is purposed, in part, for retaining the position of the eye imaging apparatus relative to the user or subject. In some embodiments, a first illuminator is attached to the inner side of the eye wearable device and is configured for directing light towards the eye of the user. Further, said light source may be configured for outputting both high intensity lighting when capturing images, and low intensity lighting in the far red wavelength spectrum of visible light for previewing retinal image locations. In addition, said an optical system may be configured for collecting light from a pupil of a subject eye being imaged and directing that light along an imaging path toward a digital image sensor.

In another embodiment, said apparatus comprises detecting a motion of the apparatus, and delaying said triggering of the flash of light from said light source and capturing the image on said digital image sensor and/or processor, until said motion has stopped. Instructions may be configured for execution on said processor, further comprising localizing, monitoring, and tracking exact landmarks and pathology of the eye including selections from the group of ocular features consisting of nevi, neovascularization, and retinal drusen or hemorrhage known from either a previous or a current examination.

In yet another embodiment the system creates the initial images by image subtraction. In this embodiment we capture one image with only the first illuminator on, a second image with only the second illuminator on and a third image with both illuminators off. The system then creates Image 1 by subtraction of the third image from the first image and creates Image 2 by subtracting the third image from the second image. This subtraction has the effect of removing ambient illumination. The preferred implementation of the system is through a still image camera. In another embodiment, a first video image in which one field has the first illuminator on and the second field has both illuminators off is captured. In the second video image, both fields have the second illuminator on. The system then subtracts field two from field one in the first image to create Image 1. Field 2 from the first image (both illuminators off) is subtracted from either of the fields of the second image to form Image 2. The system may in some cases need an illuminated, full size image in order to locate a corneal reflection that provides the position of an eye in the image. We will have that full size, fully illuminated image by using this illumination scheme.

We have described the present invention as used for imaging eyes. However, there are other applications for this invention in which an image is taken of an object that is behind a lens or other light transmissive curved structure. For example, this method and apparatus could be used to obtain images of products packaged in light transmissive packaging such as glass jars or blister packages. Such images could be used for quality control or product identification purposes. In addition, the above-described approaches may be utilized to identify a person, for example in combination with biometric identification methods such as iris identification.

The light transmissive structure is not limited to clear materials. That structure may allow passage of limited wavelengths of light which could be visible or invisible to the human eye. A common example of such a structure are the plastics used in sunglasses.

Although we have shown certain present preferred embodiments of our invention, it should be distinctly understood that the invention is not limited thereto, but may be variously embodied within the scope of the following claims.

What is claimed is:

1. An eye imaging system free from reflected light, comprising:
    a. an eye wearable device adaptable to removably attach to the eye of the user;
    b. a first illuminator attached to an inner side of the eye wearable device and adaptable to provide light towards the eye of the user;
    c. a second illuminator positioned at a distance from the first illuminator and attached to the inner side of the eye wearable device, the second illuminator configured to operate in an ON state when the first illuminator is OFF and to operate in an OFF state when the first illuminator is ON;
    d. at least one camera attached to the inner side of the eye wearable device, the at least one camera configured to capture a first image of the eye of the user when the first illuminator is in the ON state and the second illuminator is in the OFF state and a second image when the first illuminator is in the OFF state and the second illuminator is in the ON state; and
    e. a reflection removal processor in communication with the camera, the reflection removal processor adaptable to receive images captured by the at least one camera and configured to combine images that are alternatively illuminated by the first illuminator and the second illuminator utilizing a weighted sum method to construct a combined image of the eye of the user;
    f. whereby the operation of the at least one camera synchronized with the operation of the first illuminator and the second illuminator captures images of the eye and transfers to the reflection removal processor that provides real-time removal of reflections by combining the first image and the second image.

2. A system in accordance with claim 1, wherein the eye wearable device further comprises glasses.

3. A system in accordance with claim 1, wherein the illuminators emit infrared light.

4. A system in accordance with claim 1, wherein the reflection removal processor iterates through the first image and the second image pixel by pixel, generating a minimum pixel value for the first image and the second image that are combined to obtain a combined image free from reflections and/or hotspots.

5. An apparatus for creating an image of a subject positioned at a subject location which image is free of hotspots or shadows comprising:
    a. a camera for taking an image of a subject located at a subject location;
    b. a first illuminator and at least one second illuminator at a selected distance from the subject location and spaced apart from one another;
    c. an image processor connected to the camera for receiving a first image of the subject taken when the first illuminator is illuminated and the at least one second illuminator is not illuminated and receiving at least one additional image of the subject taken when the first illuminator is not illuminated and the at least one second illuminator is illuminated and combining the first image and at least one additional image utilizing a weighted sum method to produce a composite image of the subject wherein the images are each comprised of a set of pixels each pixel corresponding to a specific location relative to the subject and having a gray scale value.

6. The apparatus of claim 5 wherein there is only one second illuminator.

7. The apparatus of claim 5 further comprising a controller attached to the camera and the illuminators for turning on a selected illuminator whenever the camera captures an image of the subject.

8. An eye imaging apparatus for imaging the cornea of an eye, said apparatus comprising:
    a. an eye wearable device adaptable to removably attach to the eye of the g user, the eye wearable device for retaining the position of the eye imaging apparatus relative to the user;
    b. a first illuminator attached to an inner side of the eye wearable device configured for using a light source to direct light towards the eye of the user;
    c. wherein said light source is configured for outputting both high intensity lighting when capturing images, and low intensity lighting in the far red wavelength spectrum of visible light for previewing retinal image locations;
    d. an optical system configured for collecting light from a pupil of a subject eye being imaged and directing that light along an imaging path toward a digital image sensor and/or reflection removal processor;
    e. at least one camera for forming an image of the aperture in cornea of the eye to be inspected, the at least one camera attached to the inner side of the eye wearable device,
    f. wherein said digital image sensor and/or reflection removal processor are in communication with the camera, the digital image sensor and/or reflection removal processors adaptable to receive images captured by the at least one camera and configured to combine images that are alternatively illuminated by a first illuminator and a second illuminator utilizing a weighted sum method to construct an image of the subject.

9. The apparatus in accordance with claim 8, wherein said apparatus comprises detecting a motion of the apparatus, and delaying said triggering of the flash of light from said light source and capturing the image on said digital image sensor, until said motion has stopped.

10. The apparatus in accordance with claim 8, wherein said instructions configured for execution on the processor further comprises localizing, monitoring, and tracking exact landmarks and pathology of the eye including selected from the group of ocular features consisting of nevi, neovascularization, and retinal drusen or hemorrhage known from either a previous or a current examination.

11. A system in accordance with claim 8 wherein the eye wearable device further comprises glasses.

12. A method for creating a hotspot free image of at least a portion of the eye of a person who is positioned at a subject location, the method comprising:
   a. positioning a first illuminator and at least one second illuminator at a selected distance from the subject location and spaced apart from one another;
   b. capturing a first image of at least a portion of an eye of a person while the person's eye is illuminated by the first illuminator and not illuminated by the at least one second illuminator wherein the first image comprises a set of pixels, each pixel corresponding to a specific location relative to the person's eye and having a gray scale value;
   c. capturing at least one additional image of at least a portion of an eye of a person while the person's eye is illuminated by the at least one second illuminator and not illuminated by the first illuminator; wherein the second image comprises a set of pixels each pixel corresponding to a specific location relative to the person's eye and having a gray scale value;
   d. creating sets of pixels such that each set contains a pixel from the first image and a pixel from each additional image and all pixels in each set corresponds to a same location relative to the subject;
   e. constructing an image of the subject that is free of hotspots with a reflection removal processor by selecting one pixel from each set of pixels by choosing that pixel which has a minimum gray scale value; and
   f. wherein the processor utilizes a weighted sum method to construct an image of the subject.

13. The method of claim 12 wherein the illuminators emit infrared light.

14. The method of claim 12 wherein at least one of the illuminators emits light comprising one or more of white, red, infrared, blue, green color.

15. The method of claim 12 also comprising the step of using the image of the at least a portion of an eye of a person that is free of hotspots to identify the person.

16. The method of claim 15 wherein the person is identified using a biometric identification method.

17. The method of claim 16 wherein the biometric identification method iris identification.

18. The method of claim 12 wherein the first image is captured by at least one camera a first illuminator attached to an inner side of an eye wearable device including glasses, the first illuminator adaptable to provide light towards the eye of the user.

19. The method of claim 12, wherein capturing a first preliminary video image of the at least a portion of an eye of a person which contains a field created while the at least a portion of an eye of a person is illuminated by the first illuminator and not illuminated by the at least one second illuminator and a second field which was created while the at least a portion of an eye of a person was not illuminated by any illuminator wherein the first image is comprised of a set of pixels each pixel corresponding to a specific location relative to the at least a portion of an eye of a person and having a gray scale value and forming the first image by subtraction of the second field from the first field.

20. The method of claim 12 wherein the at least one additional image is captured by:
   a. capturing a second preliminary video image of the subject which contains two fields created while the at least a portion of an eye of a person is illuminated by the at least one second illuminator and not illuminated by the first illuminator and a second field which was created while the at least a portion of an eye of a person was not illuminated by the first illuminator and wherein the second image is comprised of a set of pixels each pixel corresponding to a specific location relative to the at least a portion of an eye of a person and having a gray scale value; and
   b. forming the second image by either subtraction from the first field of the second preliminary image of the second field of the first preliminary image or by subtraction from the second field of the second preliminary image of the second field of the first preliminary image.

* * * * *